United States Patent [19]

Thomas et al.

[11] 4,328,890
[45] May 11, 1982

[54] CONTACT LENS CONTAINER

[75] Inventors: Michael D. Thomas; Francis E. Ryder, both of Arab, Ala.

[73] Assignee: Ryder International Corporation, Arab, Ala.

[21] Appl. No.: 183,072

[22] Filed: Sep. 2, 1980

[51] Int. Cl.³ ............................................. A45C 11/04
[52] U.S. Cl. ....................................... 206/5.1; 220/401
[58] Field of Search ..................... 206/5.1, 6; 220/304, 220/401

[56] References Cited

U.S. PATENT DOCUMENTS

| | | | |
|---|---|---|---|
| 2,602,565 | 7/1952 | Regan | 220/304 |
| 3,614,959 | 10/1971 | Schollmaier et al. | 206/5.1 |
| 3,643,672 | 2/1972 | Brown | 206/5.1 |
| 3,880,278 | 4/1975 | Brown | 206/5.1 |
| 4,228,136 | 10/1980 | Thomas | 206/5.1 |

FOREIGN PATENT DOCUMENTS

| | | | |
|---|---|---|---|
| 685129 | 4/1964 | Canada | 206/5.1 |
| 40-27794 | 10/1965 | Japan | 206/5.1 |
| 313760 | 6/1929 | United Kingdom | 220/304 |

*Primary Examiner*—Joseph Man-Fu Moy
*Attorney, Agent, or Firm*—Trexler, Bushnell & Wolters, Ltd.

[57] ABSTRACT

A container or case for use in storing and sterilizing corrective contact lenses is made up of a shallow cup-like base, a cap for selectively closing the open end of the base, and a lens basket arrangement situated in the base. The lens basket arrangement includes individual lens pockets which have a central hub and spaced staves radiating from the hub, the staves including substantially coplanar inboard portions adjacent the hub and abruptly upturned outboard portions for confining a contact lens element within the respective pocket and against laterally slidably extraction therefrom.

5 Claims, 4 Drawing Figures

CONTACT LENS CONTAINER

Field of the Invention

This invention relates generally to the art of corrective contact lenses and more particularly to soft contact lenses. Specifically, the present invention relates to cases or containers for storing and sterilizing individual pairs of soft contact lenses.

BACKGROUND OF THE INVENTION

In the past, soft contact lenses have required more-or-less daily maintenance by the user in order to clean the lenses and preserve both pliability and substantial sterility. The prior art porous lenses, usually fabricated from a suitable hydrophilic resin, have conventionally been immersed in a specifically formulated saline solution within a case or container particularly adapted for the purpose, the entire case being thereafter heated in a water bath to inactivate microorganisms. Overnight storage in the gradually cooling saline solution has allowed replacement of any fugitive moisture and has ensured continuance of the desired pliability of the lenses.

More recently, flexible versions of silicone resins have been adopted for the manufacture of soft contact lenses because a greater oxygen permeability. The latter property is important to contact lens users because the cornea does not have blood supply to deliver oxygen but rather relies on oxygen absorption directly from the atmosphere. Hence, oxygen permeable silicone lenses may be worn for longer periods of time without adverse health effects. However, the silicone resins employed for contact lenses have proved comparatively hydrophobic; and therefore, special permanent coatings have been developed to make certain that the soft silicone surface is readily wet for maximizing both adhesion to the eyeball about the corneal region and comfort to the patient.

Despite their advantages from the standpoint of improved user vision, coated silicone soft contact lenses are easily scratched; and the storage cases heretofore available have promoted undesirable scratching of these lenses by encouraging the user to remove each lens from the case by means of a wiping motion which causes consequent abrasive contact between the lens and its pocket or cavity in the case.

SUMMARY OF THE INVENTION

The present invention obviates the potential for scratching or otherwise marring a soft surfaced contact lens by providing a lens case which forces the user to remove each lens using a dipping technique.

Accordingly, a general object of the present invention is to provide a new and improved lens case, particularly for soft contact lenses.

Another object of the invention is to provide a soft contact lens case which keeps each lens in its respective cavity or pocket despite inverting or rough handling of the case.

Still another object of the invention is to provide a soft contact lens case which promotes full-surface contact of each lens by the saline sterilizer fluid.

These and other objects and features of the invention will become more apparent upon a consideration of the following descriptions.

BRIEF DESCRIPTION OF THE DRAWINGS

The invention, both as to its construction and its mode of use, will be better understood by reference to the following disclosure and drawings forming a part thereof, wherein.

DESCRIPTION OF THE ILLUSTRATED EMBODIMENT

Figure 1:
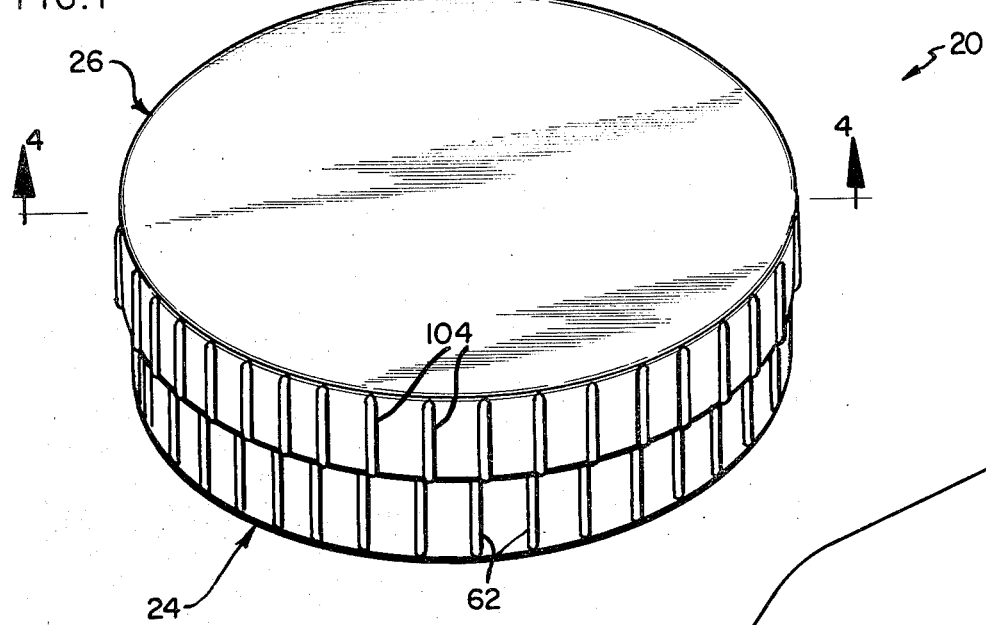
FIG. 1 is a perspective view of a contact lens container constructed according to the invention and shown with the cap screwed onto the base in the storage mode.
Figure 2:
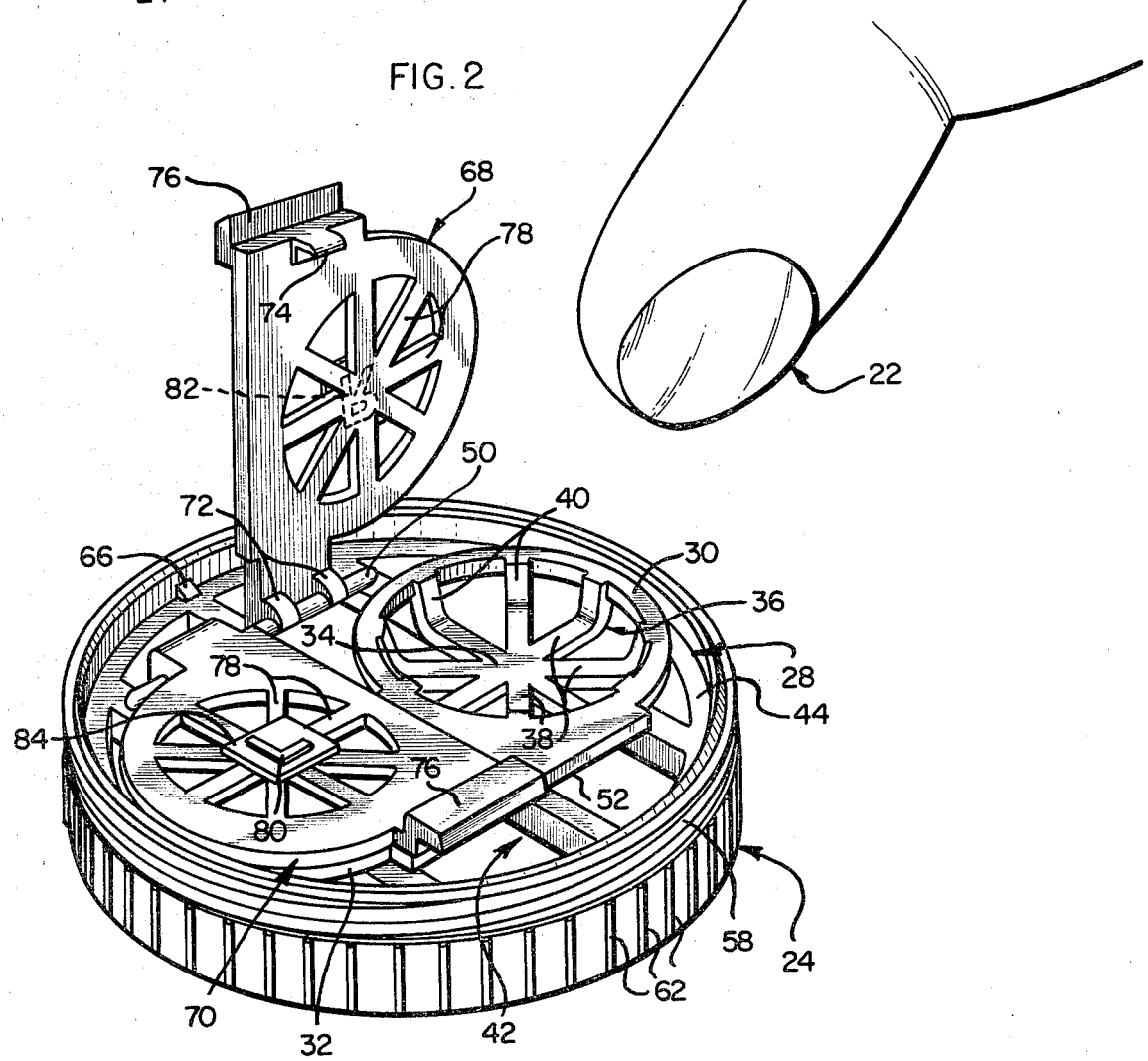
FIG. 2 is a perspective view of the container base and lens basket unit used in the container of FIG. 1, illustrating one of the lens basket covers in raised position and showing a removed contact lens adhered to a person's finger.

Referring now in detail in the drawings, specifically to FIGS. 1 and 2, a case or container indicated generally by the reference numeral 20 is arranged for use in storing and sterilizing corrective contact lenses, such as the coated, silicone soft contact lens 22 shown adhered to the tip of a person's index finger in FIG. 2. The container 20 comprises a shallow cup-like base 24, a cap unit 26 and a lens basket arrangement 28 which is situated in the base 24. The lens basket arrangement 28 includes a pair of individual lens pocket units 30 and 32, each of which has a central hub 34 and a plurality of spaced staves 36 radiating from the hub 34.

Figure 4:
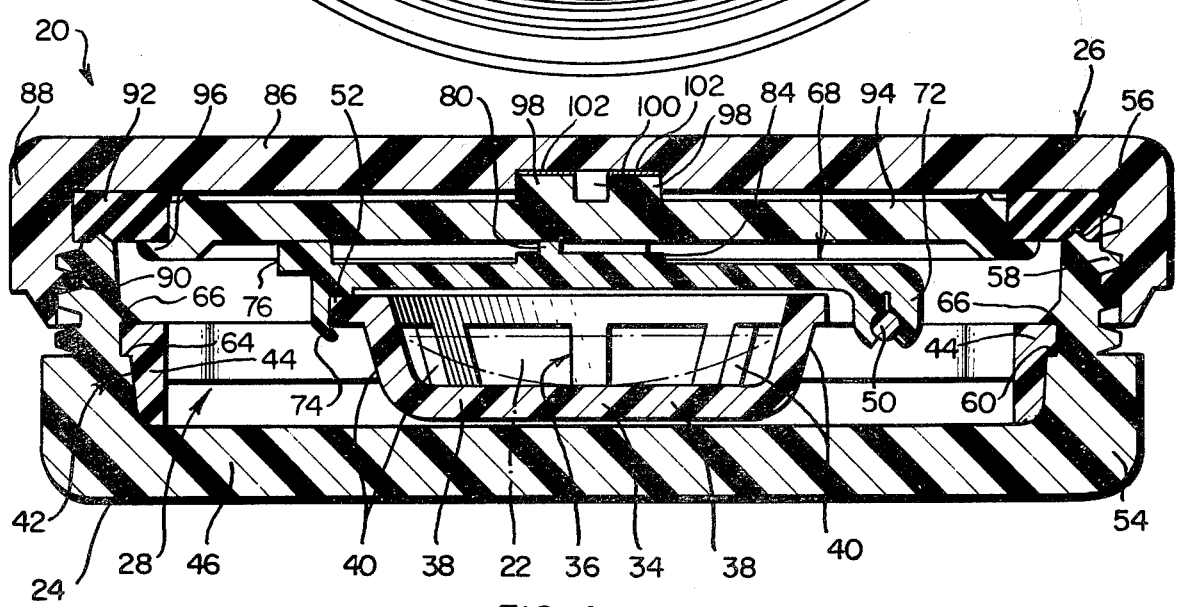
FIG. 4 is a central sectional view taken substantially along the line 4—4 of FIG. 1 with the cap in position and the lens basket covers seated in a closed condition.

In compliance with the principles of the present invention, the staves 36 include substantially coplanar inboard portions 38 adjacent the hub 34 and abruptly upturned outboard portions 40 for confining a contact lens element within its respective pocket unit and against laterally slidable extraction therefrom. Turning to FIG. 4, the outboard stave portions 40 are specifically inclined from the plane of the inboard stave portions 38 at an angle of from about seventy to about ninety degrees in order to properly confine the contact lens element within the respective pocket unit and against undesirable laterally slidable extraction therefrom. As a consequence, the contact lens must be removed using a dipping technique which avoids wiping motion and concomitant abrasive contact between the lens element and the staves of the pocket unit.

Figure 3:
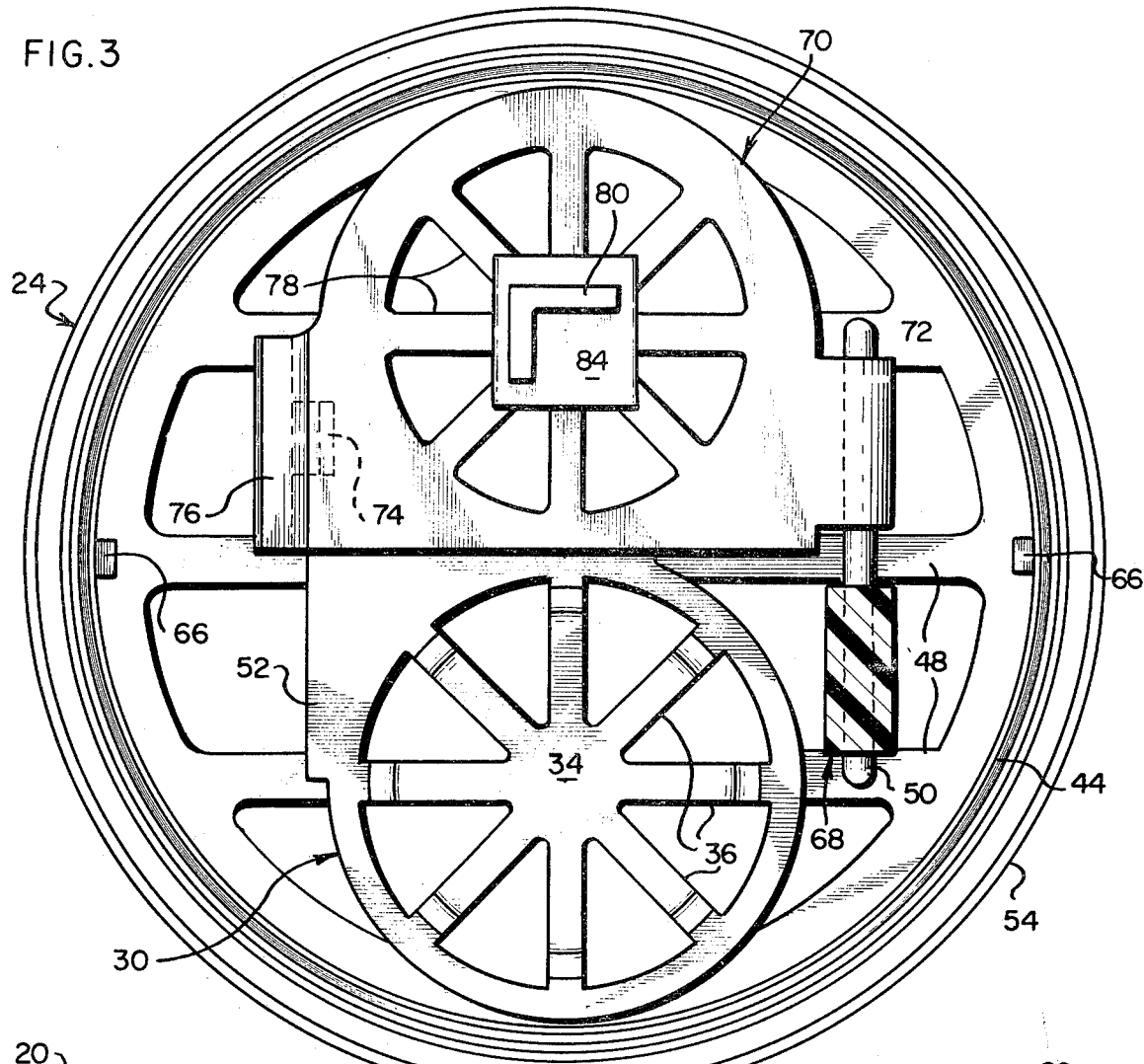
FIG. 3 is an enlarged plan view of the base and lens basket unit of FIG. 2.

Continuing with the principal reference to FIG. 4 and with secondary reference to FIGS. 2 and 3, the lens basket arrangement 28 additionally comprises an apertured cage 42 to which the individual lens pocket units 30 and 32 are confluently coupled. The cage 42 includes a peripheral rim 44 that is dimensioned to space the inboard portions of staves 36 slightly above a bottom panel 46 of the base 24 in order to promote the free flow of sterilizer fluid over and around contact lenses confined in the pocket units 30 and 32. This spacing is best shown in FIG. 4. The cage 42 also includes a suitable number of chordal ribs 48 which define spaces therebetween in order to minimize the use of material and in order to promote the free flow of sterilizer fluids. The cage 42 is additionally fashioned with an integral, cylindrical hinge pintle 50 and a rectangular latch bar 52 which is disposed parallel to the pintle, for purposes to be described more fully hereinafter.

In addition to the circular bottom panel 46, the base 24 includes an endless sidewall 54 having an annular, pyramidally shaped top edge 56, an external thread 58 adjacent the top edge 56, a radially inwardly extending shelf or ledge 60, and external knurling ribs 62. The rim 44 of lens basket arrangement 28 is provided with a radially outwardly extending shelf or ledge 64 which cooperates with the ledge 60 in positioning the lens basket arrangement 28; and the sidewall 54 of base 24 includes a suitable number of radially inwardly extending keeper lugs 66 which hold the ledges 60 and 64 in engagement and which are downwardly inwardly declined in order to lead the lens basket arrangement into snapfit assembly with the base 24.

In addition to the cage 42, the lens basket arrangement 28 includes individual swingable covers 68 and 70 for the respective lens pocket units 30 and 32. The covers 68 and 70 are integrally fashioned with respective split, resilient hinge knuckles 72 which rotatably grip the hinge pintle 50. Moreover, each of the covers 68 and 70 includes a latch strike 74 which releasably and resiliently snaps over the latch bar 52 to lock or secure the cover in position confining a contact lens element within the respective lens pocket unit. A lift extension 76 conveniently serves as a grip or handle for each of the covers 68 and 70. Moreover and in compliance with the present invention, the covers 68 and 70 include spaced-apart, radial rib elements 78 which define apertures therebetween for passing lens-conditioning fluid through the lens pocket units.

In further compliance with the present invention, the covers 68 and 70 are advantageously provided with distinguishing indicia; and in order to assist a vision-impaired person planning to install his or her contact lenses, these distinguishing indicia are arranged to be tactily identifiable. In the illustrated embodiment, raised or embossed letters "L" and "R" are indicated respectively by the reference numerals 80 and 82 and are disposed on respective, central platforms 84 attached to the covers 68 and 70.

Continuing with particular reference to FIG. 4, the cap unit 26 includes a circular top panel 86 which terminates in an endless sidewall 88. An internal thread 90 is fashioned on the inner surface of sidewall 88 for progressive engagement and disengagement with the thread 58 of base 24. Desirably, the cap unit 26 and the base 24 are capable of being screwed together with a fluid-tight seal therebetween. Accordingly and in compliance with a further feature of the invention, an annular gasket 92 is mounted in the cap unit 26 for compressible engagement by the annular top edge 56 of the base 24, the gasket 96 being held in place by a planar insert disc 94 which is provided with a radially outwardly extending lip 96 for partially overlappingly engaging the gasket. Furthermore, the disc 94 includes centrally disposed nubs or projections 98 which fit into an appropriately shaped recess 100 in the top panel 86 where fusion joints 102 are thermally created in order to make permanent the attachment of the disc and the top panel of the cap unit. Finally, companion knurling ribs 104 are raised from the exterior surface of cap sidewall 88, as is best seen in FIG. 1, for cooperating with the basewall ribs 62 in unscrewing the cap unit 26 from the base 24.

For purposes of affording a more complete understanding of the invention, it is advantageous now to provide a functional description of the mode in which the component parts operate.

Assuming that a user of contact lens elements desires to commit his or her corrective lenses to overnight storage and sterilization, the cap 26 will be unscrewed from the base 24 and the covers 68 and 70 will be lifted. The individual lens elements will then be removed from the person's eyes and deposited in the lens pocket units 30 and 32, making sure that the left lens is placed in the pocket unit 32 and the right lens element in the pocket unit 30. The covers 68 and 70 will then be lowered into closing condition with the strikes 74 engaging over the corresponding latch bars 52. A suitable quantity of sterilizing fluid will then be poured into the base 24, immersing the contact lens elements 22 to a suitable depth. It will be appreciated that the sterilizing fluid will have efficient access to the lens elements because of the spacing of the staves 36 of the lens pocket units, the spacing of the radial ribs 78 in the covers 68 and 70, and the open structure of the cage 42. The spacing of the coplanar portions 38 of the staves 36 above the bottom panel 46 of the base 24 furthers the free flow of the sterilizer fluid into contact with the respective lens elements.

After the cap unit 26 is screwed onto the base 24, the entire lens case or container 20 can be immersed in a heated water bath to inactivate microorganisms, subject the surfaces of the contact lens elements to lavage, and expose the lens elements to a source of water to replace lost moisture.

Upon arising the next morning, the user will merely unscrew the cap unit 26 from the base 24 and, relying on the indicia 80 and 82 either visually or tactily, will raise the approriate lens basket cover and select the proper lens element for each eyeball. Each lens element will then be removed using a dipping action with a finger tip, thus avoiding the possibility of scratching the susceptible surface of the lenses. The shaping of the staves of the lens pockets forces the user to employ this highly desirable mode of lens extraction. The lens case or container will then be rinsed and reassembled in preparation for its next utilization.

While a particular embodiment of the invention has been shown and described, it should be understood, of course, that the invention is not limited thereto since many modifications may be made; and it is, therefore, contemplated to cover by the present application any such modifications as fall within the true spirit and scope of the invention.

The invention is claimed as follows:

1. A container for use in storing corrective contact lenses emersed in a lens conditioning fluid, comprising; a shallow cup-like base having an open-end and a bottom panel opposite said open end; cap means for selectively closing the open end of said base; and lens basket means disposed in said base, said lens basket means including cage means having a rim with a pair of individual lens pocket means formed integral with said cage means and disposed in side-by-side relation interiorly of said rim, said lens pocket means having a central hub and spaced staves radiating from said hub to provide an open latice construction for said lens pocket means, said staves including substantially coplanar inboard portions adjacent said hub and abruptly upturned outboard portions inclined from the plane of said inboard stave portions and at angle from about 70 to about 90 degrees for confining the contact lens element within said lens pocket means and against laterally slidable extraction of the lens element therefrom, said cage means further including a pair of integral hinged pintles with aperture cover means for said lens pocket means pivotally connected to said pintles, said cage means also including a plurality of chordal ribs joining said lens pocket means to said rim thereby providing an open latice construction about said lens pocket means, and said rim extending below said lens pocket means to engage said bottom panel thereby spacing said lens pocket means above said bottom panel whereby the open latice construction of said lens pocket means and said cage means, the aperture cover means and the spacing of said lens pocket means above said bottom panel all serve to promote the free flow of lens conditioning fluid to the lenses carried by said lens pocket means.

2. A container for use in storing and sterilizing corrective contact lenses according to claim 1 wherein said cover means includes tactily identifiable indicia means.

3. A container for use in storing and sterilizing corrective contact lenses according to claim 1 wherein said base includes a continuous edge encompassing said open end; and wherein said cap means includes a gasket engageable with said edge and retention means for positively positioning said gasket.

4. A container for use in storing and sterilizing corrective contact lenses according to claim 3 wherein said retention means includes a planar insert and fusion joint means for attaching said insert.

5. A container for use in storing and sterilizing corrective contact lenses according to claim 4 wherein said insert has an outwardly extending lip for partially overlappingly engaging said gasket.

* * * * *